United States Patent [19]
Farivar et al.

[11] Patent Number: 5,223,309
[45] Date of Patent: Jun. 29, 1993

[54] ION IMPLANTATION OF SILICONE RUBBER

[75] Inventors: Robert S. Farivar, Cambridge; Piran Sioshansi, Lincoln, both of Mass.

[73] Assignee: Spire Corporation, Bedford, Mass.

[21] Appl. No.: 910,777

[22] Filed: Jul. 8, 1992

Related U.S. Application Data

[63] Continuation of Ser. No. 728,098, Jul. 10, 1991, abandoned.

[51] Int. Cl.$^5$ ............................................. B05D 3/06
[52] U.S. Cl. .................................. 427/525; 427/296; 427/527
[58] Field of Search ................... 427/38, 296, 525, 527

[56] References Cited

U.S. PATENT DOCUMENTS

| | | | |
|---|---|---|---|
| 3,434,869 | 3/1969 | Davidson | 117/94 |
| 4,100,309 | 7/1978 | Micklus et al. | 128/844 |
| 4,693,760 | 9/1987 | Sioshansi | 148/4 |
| 4,743,308 | 5/1988 | Sioshansi et al. | 148/4 |
| 4,743,493 | 5/1988 | Sioshansi et al. | 428/217 |

OTHER PUBLICATIONS

M. S. Dresselhaus et al. "Ion Implantation of Polymers" Mat. Resources Soc. Symp. Proc., vol. 27 (1984) pp. 413-422.

Yoshiaki Suzuki et al. "Effects of Ion Implantation on Protein Absorption onto Silicone Rubber." Mat. Res. Soc. Symp. Proc., vol. 110, MRS, 1989.

Primary Examiner—Bernard Pianalto
Attorney, Agent, or Firm—Morse, Altman, Dacey & Benson

[57] ABSTRACT

A process to improve the surface properties of products made, at least in part, from silicone rubber is disclosed. The products find uses in industrial and medical device applications, such as drug-pump seals and valves, membranes, mammary prostheses, artificial heart diaphragms, pacemaker lead insulation and the like. The process is designed to change the silicone rubber's surface to one that is characterized by low friction, being antithrombotic, inkable, more wear resistant and deformable, and also being hydro-compatible. The process includes subjecting the product's silicone rubber surface to ion bombardment with gaseous ions that diffuse out with doses and at energy levels at least about 3E14 ions/cm$^2$ at 80 keV.

7 Claims, 2 Drawing Sheets

ION IMPLANTATION OF SILICONE RUBBER

This is a continuation of application Ser. No. 07/728,098 filed on Jul. 10, 1991 abandoned.

BACKGROUND OF THE INVENTION

1. Field of the Invention

The present invention relates generally to ion implantation of silicone rubber and, more importantly, to an ion implantation process for silicone rubber designed to change the silicone rubber's surface to one characterized by low friction, being antithrombotic, inkable, wear resistant, deformable and hydro-compatible.

2. The Prior Art

Silicone rubbers find important and varied uses in industrial and medical device applications. In the medical field, manufacturers use silicone rubber, inter alia, in forming seals and valves for many groups, for membranes for insulators in electrostimulation devices and pacemakers, for artificial heart diaphragms, in penile implants, for mammary prostheses and the like. Silicone rubber is favored in the applications because it is biocompatible, is permeable to gases, is easily molded and is highly deformable.

Silicone rubber is not without its drawbacks, however. It evinces high friction against metals, other polymers and itself. Such high friction requires the addition of lubricating agents, such as fluorosilicone oil, in many applications. When the addition of lubricating agents is not possible, as in certain in-vivo implants, it often leads to premature failure due to abrasive wear and/or cracking. This property of high friction in silicone rubbers is the result of the surface morphology and of the surface energy. During their molding, whether by companion, transfer or injection molding, silicone rubber products at times acquire a rough surface morphology due to the compressive stresses built into them from the molding operation. Secondly and more importantly, certainly in medical device applications, bodily tissue and cells have a tendency to stick and stay stuck onto the silicone rubber surface, whence they may enter the vascular system, causing occlusion, clotting and strokes Since silicone rubber is non-planar and hydrophobic due to its surface energy, it has not been easily inkable.

Attempts to improve the surface properties of silicone rubber products have, for the most part, concentrated on providing suitable coatings therefor. Such coatings have included hydrogel or fluorosilicone lubricants, sulfonation processes or the employment of special adhesives. See U.S. Pat. Nos. 4,100,309 and 4,119,094 of Michael J. Micklus et al., "Coated Substrate Having a Low Coefficient of Friction Hydrophilic Coating and a Method of Making the Same". Each of these coatings introduces, however, "shelf-life" problems to the silicone rubber products. Lubricants used in implanted drug-pumps wear off with time and enter the vascular system, being the source of potentially life-threatening complications. Hydrogel coatings also can detach from silicone rubber devices due to excessive heat and/or hydration, heralding a wealth of complications and device failures. And the sulfur groups from the applied sulfonation processes severely limit the shelf-lives of the silicone rubber devices.

More recently, a Japanese corporation, Terumo Corporation, has investigated the effects of ion implantation on plasma protein adsorption onto silicone rubber sheets. See Yoshiake Suzuki et al, "Effects of Ion Implantation on Protein Adsorption onto Silicone Rubber," *MRS Symposium Proceedings* (1989), vol. 110, pp. 669–679. The article notes in the Abstract, inter alia, that "Ion implantation causes the surface roughness to increase by 1–5 times," see lines 5–6 of the Abstract. The Abstract also states that "The results of XPS measurements showed that implanted elements were incorporated in a gaussian like distribution and host elements were redistributed in the polymer matrix." See Abstract, lines 10–12. Our aims are opposed to both of those observations. We are interested in reducing surface roughness to achieve low surface friction and smoothness. We also are interested in improved wear resistance and improved anti-thrombogenicity. We are not interested in improving plasma protein adsorption onto the surfaces of the ion implanted silicone rubbers, however, which is a sort of protective coating.

SUMMARY OF THE INVENTION

It is a principal object of the present invention to overcome the above disadvantages by providing a process for improving the surface properties of silicone rubber products so as to enhance their use in the medical devices field.

More specifically, it is an object of the present invention to provide an economical, reliable and reproducible process for advantageously changing the surface characteristics of silicone rubber products so as to render them more acceptable for implantation. Representative silicone rubber products include drug-pump seals and valves, membranes, mammary prostheses, artificial heart diaphragms, pacemaker lead insulation, penile implants and the like. The inventive process essentially is designed to change the silicone rubber's surface to one characterized by low friction, by being antithrombotic, inkable, wear resistant, deformable, and by being hydro-compatible. The process essentially comprises the mounting of a product made, at least in part, from silicone rubber within a suitable vacuum chamber of an ion implantation device, creating a vacuum of at least about $10^{-3}$ torr therein, and exposing the product's surface to an ion beam of gaseous ions that will eventually diffuse out of the product's surface. Preferably, the ion beam is one delivering a dose of ions ranging from about 3E14 ions/cm$^2$ to about 3E17 ions/cm$^2$ at a particle energy ranging from about 0.5 keV to about 200 keV, and with a current density from about 0.01 uA/cm$^2$ to about 10.00 uA/cm$^2$. Preferably, the gaseous ions are generated from one of a group consisting of nitrogen, helium, hydrogen, argon, oxygen, neon, fluorine, and kryton, xenon, $CF_4$, $CH_4$ and $CO_2$.

Other objects of the invention will in part be obvious and will in part appear hereafter.

The invention accordingly comprises the process and the resultant product of the present disclosure, its steps, components, parts and their interrelationships, the scope of which will be indicated in the appended claims

BRIEF DESCRIPTION OF THE DRAWINGS

For a fuller understanding of the nature and objects of the present invention, reference is to be made to the following detailed description, which is to be taken in connection with the accompanying drawings, wherein.

DETAILED DESCRIPTION OF THE PREFERRED EMBODIMENT

Figure 1:
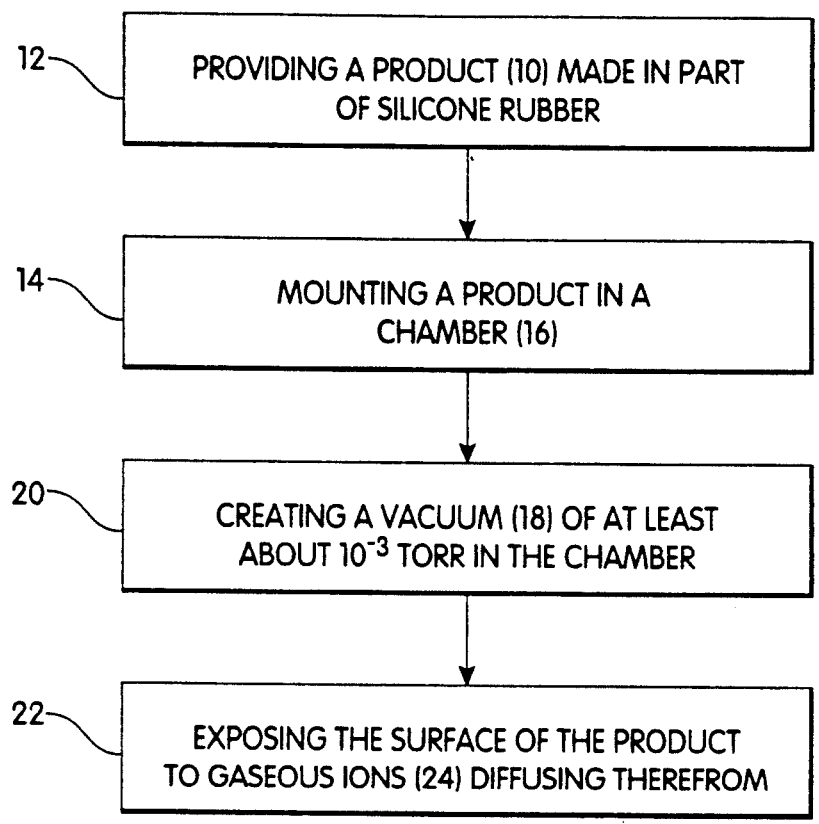
FIG. 1 is a flow diagram graphically illustrating the essential steps of the inventive process.

An ion implantation process for the improvement of the surface properties made at least in part of silicone rubber is generally illustrated in a flow diagram of FIG. 1. The products of interest here find important and widespread uses in industrial and medical device applications, including drug-pump seals and valves, membranes, mammary prostheses, artificial heart diaphragms, pacemaker lead insulation, enteric feeding tubes, endocardial leads, catheters, dilators, wound drains and the like. The invention process is designed to advantageously affect the surface of the silicone rubber to become a smooth glassy one that is characterized by a low coefficient of friction closer to that of teflon, by being non-thrombogenic, being inkable, wear resistant, deformable and hydro-compatible. Such surface properties in medical devices, designed for entry into the human body are very important. For the insertion of a device with a low friction coefficient greatly reduces the trauma to the body tissue involved, reducing thereby the chance for infection. In addition to reducing thrombin levels, devices with a low friction coefficient also are likely to prevent fibrin formation. The device's surface affinity for albumin also is important re platelet adhesion, aggregation and/or release into the vascular system. As known, fibrinogen is undesirable scar tissue while albumin simulates the internal endothelialization of the body, preventing the onset of clotting.

As known, the coefficient of friction of teflon in its dry condition is 0.16, wet 0.15; of latex rubber when dry 0.29, wet 0.26; but of silicone rubber in the dry condition it is a very high 1.53 and still a too high 1.50 when wet. Silicone rubber is favored however, since it is biocompatible, is permeable to gases, is easily molded, including by injection molding, and is highly deformable. The process of the invention is designed to obviate the above drawbacks to the more widespread use of silicone rubber devices in a simple, economical, and reproducible manner and without the use of lubricating agents or of hydrogel coatings. Hydrogel coatings are characterized by the formation of colloids in which the disperse phase has combined with the continuous phase to produce a viscous jelly like surface.

The silicone rubber products, as above enumerated, are subjected to an ion implantation process characterized in that the products' silicone rubber surface is bombarded with gaseous ions that eventually diffuse out of the surface and leave in place a smooth glassy surface. This smooth glassy surface of the treated silicone rubber against treated silicone rubber possesses a low coefficient of friction closer to that of teflon, i.e., about 0.16 than to the surface of an untreated silicone rubber, i.e., about 1.53. The smooth glassy surface also is non-thrombogenic and, as a consequence, combines the inherent advantageous properties with these newly-acquired ones to produce a highly desirable product for medical device applications. The smooth glassy surface also is found to be inkable and hydro-compatible. The invention thus adapts the ion implantation method to the advantageous ion implantation of silicone rubber products so as to improve their surface properties.

One of the co-inventors and the common assignee herein have been involved in employing ion implantation for various uses. In U.S. Pat. No. 4,693,760, granted to Piran Sioshansi on Sep. 15, 1987, an ion implantation process for preventing surface discoloration in orthopaedic implants made of titanium and its alloys is disclosed. In U.S. Pat. No. 4,743,493, granted to Piran Sioshansi et al on May 10, 1988, an ion implantation process to enhance the surface hardness and resistance to chemical attack of plastics is disclosed. And in U.S. Pat. No. 4,743,308, granted to Piran Sioshansi et al on May 10, 1988, an ion implantation process to inhibit the corrosion of metal alloys is disclosed.

The process of the invention is designed to be employed on individual products formed either in toto or in part of silicone rubbers Silicone rubbers have a different type of polymer structure from any of the other types of rubbers. For in lieu of a chain structure involving a long chain of carbon atoms, silicone rubbers feature a sequence of silicon and oxygen atoms in a siloxane structure. A siloxane structure generally is represented by a formula:

Formula 1

A representative siloxane component, prior to curing, is shown by a formula:

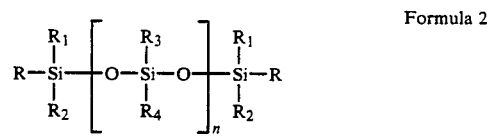

Formula 2 wherein each of R, R1 and/or R2 is one of the group such as an ester moiety, an alchohol moiety, an acetoxy moiety, an acrylic moiety and the like that are involved in the crosslinking, curing and polymerizing of the silicoxane component. R3 and R4 as well as R1 and R2, can each be one of the aliphatic or aromatic groups such as methyl, ethyl, propyl, phenyl or substituted aliphatics or aromatics containing halogen moieties or other groups. This general formula represents a siloxane component that can react with itself with or without the presence of moisture and/or a catalyst in order to crosslink or polymerize into the silicone elastomer. If at least the R groups are alcohol moieties, the silicone elastomer can be formed by reaction with a suitable crosslinking component. Silicone rubber is customarily vulcanized by means of peroxides. The peroxides remove some of the hydrogen atoms from the methyl ($CH_3$) groups on the silicon atoms, permitting the carbon atoms of two adjacent chains to couple and form crosslinks.

An exemplary silicone elastomer or rubber is a siloxane condensation reaction product, the principal reactants of which include a silicone moiety:

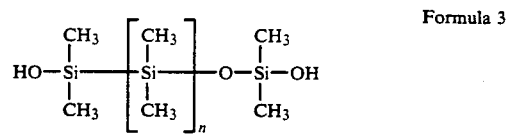

Formula 3 wherein n has an average value of greater than 100.

Another principal reactant is an acetoxy silane cross-linker of the formula:

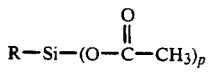

Formula 4 wherein p is 1, 2 or 3. The exemplary siloxane of this type is poly(dimethyl siloxane). Polymeric siloxanes are generally known and are commercially available, for example, from Dow Corning Corporation. For a closer description of siloxanes, see U.S. Pat. No. 3,434,869.

The siloxane structure results in a flexible chain, with weak interchain forces. As a consequence silicone rubbers also are noted for tolerating well a wide range of temperatures with no adverse physical or chemical effects. Silicone rubbers also show no tendency to crystallize when stretched. Due to their weak interchain forces, silicone rubbers must be reinforced by a pigment, which pigment usually is a fine silica powder.

Essentially, the process of the invention is graphically illustrated in FIG. 1. A product 10, made in whole or in part from silicone rubber (any type or kind of silicone rubber) is first provided 12 since the inventive process is designed to be employed on finished individual final products formed of silicone rubbers, as above described, and destined for use in the industrial or medical device application fields. The product 10 or rather preferably a plurality of such products is mounted 14 in a suitable ion implantation chamber 16. A vacuum 18 of at least about $10^{-3}$ torr is created 20 in the chamber 16. Thereafter, the surface of the product 10 is exposed 22 within the chamber to bombardment by a gaseous ion 24 that diffuses out of the product shortly following the termination of the ion bombardment.

The ion bombardment by the gaseous ions 24 favorably effects changes in the surface properties of the silicone rubber product 10, as already stated above. The ion bombardment by the gaseous ions 24 does effect only minimal changes in the bulk of the product, however. As mentioned, the bombardment of the surface of the silicone rubber product 10 by the gaseous ions 24 causes the surface, for the most part, to become a glassy smooth one, characterized by a low coefficient of friction closer to that of teflon from one of an untreated silicone rubber. At times, the surface does crack as a result of the thermal process of $i^2$. The ion bombarded surface of the product 10 also is non-thrombogenic, it effectively prevents fibrin formation, is inkable, wear resistant, deformable, and hydro-compatible. The thus treated silicone rubber product effectively combines the desirable bulk properties of silicone rubber with the desirable surface properties of a material, such as teflon The processing parameters of the inventive process and the respective ranges thereof are as follows. The negative pressure, i.e., the vacuum 18 within the ion implantation chamber 16 can range from about $10^{-3}$ torr to about $10^{-8}$ torr, and preferably is about $10^{-6}$ torr The ion beam comprised of the gaseous ions 24 has a dose ranging from about 3E14 ions/cm² to about 3E17 ions/cm², at a particle energy ranging from about 0.5 keV to about 200 keV, and with a current density ranging from about 0.01 uA/cm² to about 10.00 uA/cm²: The ion bombardment with the gaseous ions 24 preferably extends for a time period at least about 5 minutes to about ten hours. The gaseous ions 24 are designed to penetrate the surface of the silicone rubber product 10 to a depth of about 0.1 microns.

Figure 2:
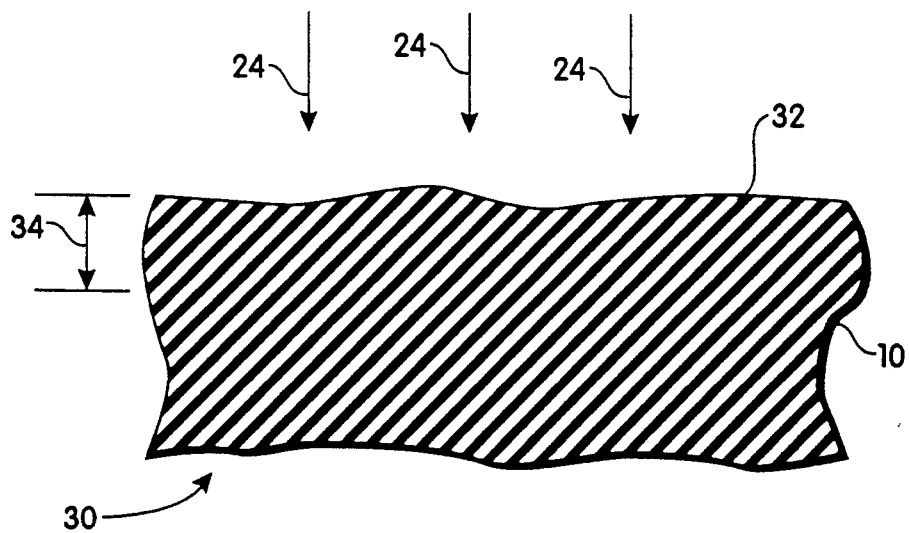
FIG. 2 is a fragmentary section, on an enlarged scale, of a silicone rubber product subjected to the process of the invention.

A fragmentary section 30, on an enlarged scale, of the silicone rubber product 10 that has been subjected to the process of the invention is illustrated in FIG. 2. As shown, an ion beam of gaseous ions 24 strikes the surface 32 of the product 10 and penetrates at a preferred distance of about $1/10^{th}$ of a micron beneath that surface 32, as exemplified by an arrow 34. The gaseous ions 24 that have penetrated below the surface 32 of the product 10 have since diffused out of the product 10, hence are not shown therein. The ion implantation treatment also increases the surface energy of the surface 32 of the product 10, rendering it more hydro-compatible, as well as more deformable and more wear resistant.

Figure 3:
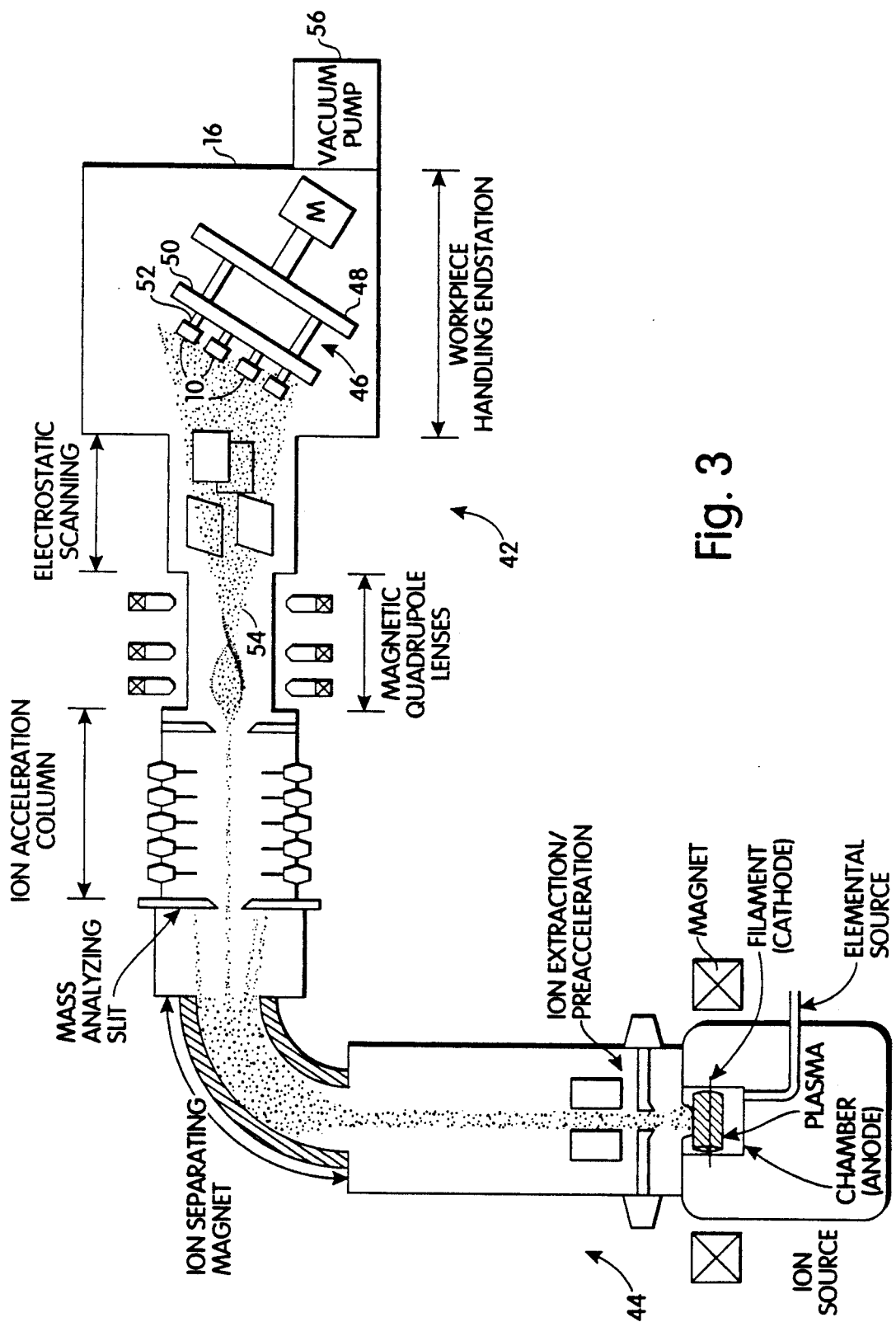
FIG. 3 is a schematic view of an ion beam implanter adapted to practice the inventive process.

The process of the invention designed to improve the surface properties of silicone rubber products 10 is preferably carried out in the chamber 16 of a specially designed endstation 42 of a suitable high current ion implanter 44, such as a Varian-Extrion 200 kV implant an Eaton-Nova implanter or a like instrument illustrated in FIG.3. This ion implanter 44 can be the same as, or an adaptation of the one illustrated in and described in said U.S. Pat. No. 4,693,760, granted Sep. 15, 1987 and assigned to the common assignee, Spire Corporation of Bedford, Mass. The analyzing magnet can be omitted from the ion implanter 44.

Within the implantation chamber 40, a suitable fixture 46 is mounted on a base 48 designed for rotation by a suitable motor (M) and for cooling a base plate 50, preferably made of aluminum or titanium, by means not shown. On the base plate 50 preferably are mounted a plurality of appropriately shaped workpiece holders 52, each preferably consisting of plates designed to hold a multiplicity of parts and also preferably made of aluminum or titanium. These workpiece holders 52 are designed to hold securely a plurality of products 10 and directly to expose these silicone rubber products 10 to an incoming ion beam 54 of gaseous ions. It is to be understood that the shape of the particular workpiece holders 52 secured to the base plate 50 will of course depend upon the shape of the particular silicone rubber products 10 worked on at that time.

With the silicone rubber products 10 duly mounted within the chamber 16, the next step of the process of the invention involves the creation of a proper vacuum environment within the implantation chamber 16. This is effected by means of a vacuum pump 56 operatively connected to the chamber 16. With the aid of the pump 56, the implantation chamber 16 is preferably evacuated to a vacuum pressure of at least $10^{-3}$ torr. Preferably, the vacuum pump 56 should be of an oil-free type so as to avoid the possibility of introducing surface contamination onto the part to be ion implanted.

The silicone rubber products 10 are then exposed to an ion beam 54 of ions so as to modify their surface characteristics. Preferably, the ion beam 54 possesses an energy from about 0.5 keV to about 200 keV, delivering a dose from about $3 \times 10^{14}$ to about $3 \times 10^{17}$ ions per square centimeter. The above mentioned ion beam energy and ion dose are intended to achieve a current density on the respective surfaces of the products 10 from about 0.01 microampre per square centimeter to about about 10.00 microampere per square centimeter. The ion implantation process of the invention is effected over a time period from about 5 minutes to about 10 hours, depending on the desired surface characteristics to be achieved by a selected combination of ion dose and ion beam current energy.

We have found that:

1. For a given ion beam energy level, increasing the ion dose will result in a surface with superior "performance," i.e., characterized by low friction, non-thrombogenicity, desired surface energy, being inkable, wear resistant, more deformable and being being hydro-compatible.

2. For a given ion beam energy, increasing the current density will result in degradation of the "performance" in the surface.

3. Lowering the energy generally improves the "performance" in the surface.

4. Increasing the dose generally improves the "performance" in the surface. However, there is a saturation limit above which "performance" in the surface will not improve.

Thus it has been shown and described a process for the ion implantation of silicone rubber materials with gaseous ions designed to improve their surface characteristics notably their coefficients of friction and their thrombogenicity and their wettability, which process and resultant product satisfy the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. A process of improving the surface properties of silicone rubber products by reducing their surface roughness comprising:
   (a) providing a product at least in part from silicone rubber;
   (b) subjecting said product to ion bombardment with a gaseous ion so as to reduce said product's surface roughness and its coefficient of friction;
   (c) said ion bombardment being effected with a dose of at least about 3E14 ions/cm$^2$ at a particle energy of about 80 keV;
   (d) sad gaseous ion being one of a group consisting of nitrogen, helium, hydrogen, argon, oxygen, neon, flourine, krypton, xenon, CF$_4$, CH$_4$, and CO$_2$;
   (e) said ion bombardment effecting a lasting change in the surface energy of said ion bombarded surface.

2. The process of claim 1 wherein said product is one or more of the group including: drug-pump seals, drug-pump valves, membranes, electro-stimulation devices, pacemaker lead insulation, artificial heart diaphragms, catheters, mammary prostheses, penile implants, vascular grafts and finger joints and assorted medical tubing.

3. The process of claim 1 wherein said dose ranges from about said 3E14 ions/cm$^2$ to about 3E17 ions/cm$^2$, wherein said reduced coefficient of friction approximates that of latex rubber, wherein said ion bombardment is effected with a current density from about 0.01 uA/cm$^2$ to abut 10.00 uA/cm$^2$, wherein said reduced coefficient of friction helps to reduce fibrin adsorption on said product's surface, and wherein said gaseous ion is an isotopically pure ion specie of one of said group.

4. A process of effecting lasting changes in the surface morphology and surface energy of silicone rubber products comprising:
   (a) providing a product made at least in part from silicone rubber;
   (b) mounting said product in a chamber;
   (c) creating a vacuum of at least about 10$^{-3}$ torr in said chamber;
   (d) exposing the surface of said product to an ion beam of gaseous ions so as to reduce the surface roughness and the coefficient of friction of said surface, with said coefficient of friction approximating that of latex rubber;
   (e) said ion beam having a dose varying from about 3E14 ions/cm$^2$ to about 3E17 ions/cm$^2$ at a particle energy ranging from about 0.5 keV to about 120 keV, and with a current density ranging from about 0.01 uA/cm$^2$ to about 10.000 uA/cm$^2$;
   (f) said ion beam being composed of an isotopically pure ion specie;
   (g) said exposing said surface of said product to said ion beam, being for a time period from about 5 minutes to about 10 hours.

5. The process of claim 4 wherein said product is one or more of the group including: drug-pump seals, drug-pump valves, membranes, electro-stimulation devices, pacemaker lead insulation, artificial heart diaphragms, catheters, mammary prostheses, penile implants, vascular grafts and finger joints and assorted medical tubing.

6. The process of claim 4 wherein said gaseous ions being one of a group consisting of nitrogen, helium, hydrogen, argon, oxygen, neon, fluourine, krypton, xenon, CF$_4$, CH$_4$ and CO$_2$.

7. The process of claim 4 wherein said exposing the surface of said product to said ion beam effects a lasting increase in the surface energy of said surface rendering said surface to be more wear resistant, deformable, and hydro-compatible.

* * * * *